United States Patent [19]

Nakao et al.

[11] 4,007,177

[45] Feb. 8, 1977

[54] CEPHALOSPORIN DERIVATIVES

[75] Inventors: Hideo Nakao; Hiroaki Yanagisawa; Mitsuo Nagano; Bunji Shimizu; Masakatsu Kaneko; Shinichi Sugawara, all of Tokyo, Japan

[73] Assignee: Sankyo Company Limited, Tokyo, Japan

[22] Filed: Nov. 14, 1974

[21] Appl. No.: 523,819

[30] Foreign Application Priority Data

Nov. 26, 1973 Japan .......................... 48-132441
Nov. 26, 1973 Japan .......................... 48-132442
Dec. 18, 1973 Japan .......................... 48-142097
Aug. 12, 1974 Japan .......................... 49-92129
Aug. 12, 1974 Japan .......................... 49-92131

[52] U.S. Cl. .................. 260/243 C; 260/307 H; 260/345.7; 260/349; 260/465.4; 260/481 R; 260/526 S; 260/544 Y; 424/246
[51] Int. Cl.² ............. C07D 501/50; C07D 501/56
[58] Field of Search .................. 260/243 C

[56] References Cited

UNITED STATES PATENTS

| | | | |
|---|---|---|---|
| 3,530,123 | 9/1970 | Takano et al. | 260/243 C |
| 3,840,531 | 10/1974 | Greene et al. | 260/243 C |
| 3,883,520 | 5/1975 | De Marinis | 260/243 C |
| 3,887,549 | 6/1975 | Christensen | 260/243 C |
| 3,905,963 | 9/1975 | Webber | 260/243 C |
| 3,920,639 | 11/1975 | Dolfini | 260/243 C |

OTHER PUBLICATIONS

Cama et al., J. Am. Chem. Soc., v. 94(4) pp. 1408–1410 (1972).

Primary Examiner—Nicholas S. Rizzo
Assistant Examiner—Diana G. Rivers
Attorney, Agent, or Firm—Flynn & Frishauf

[57] ABSTRACT

A compound of the formula

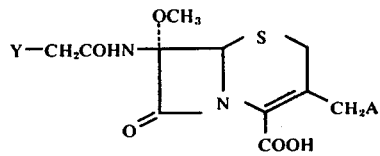

wherein A represents acetoxy group, carbamoyloxy group or (1-metyl-1H-tetrazol-5-yl)thio group and Y represents propargylthio group, azidomethylthio group, 2-hydroxyethylthio group, 3-isoxazolyloxy group, 3-isoxazolylthio group, methylsulfonyl group, ethylsulfonyl group, 2-cyanoethyl-sulfonyl group or sydnon-3-yl group and nontoxic pharmaceutically acceptable salts thereof are prepared by a process which comprises reacting a compound of the formula

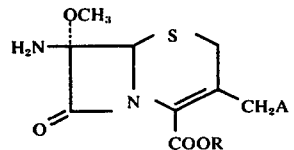

wherein R represents a protective group for a carboxyl group and A has the same meaning as defined above with a carboxylic acid of the formula

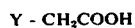

wherein Y has the same meaning as defined above or a reactive derivative thereof to give a compound having the formula

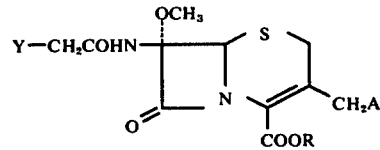

wherein A, R and Y have the same meanings as defined above and removing the protective group for the carboxyl group from said compound.

The compounds are antibacterial agents.

5 Claims, No Drawings

CEPHALOSPORIN DERIVATIVES

This invention relates to novel 7α-methoxycephalosporin derivatives of value as antibacterial agents, as nutritional supplements in animal feeds and as therapeutic agents in poultry and animals, including human, in the treatment of infectious diseases caused by Gram-positive and Gram-negative bacteria.

Certain 7α-methoxycephalosporin derivatives have been disclosed in Japanese Patent Provisional Publication Nos. 3286/71 and 931/72, the Journal of the American Chemical Society, vol. 94, P. 1408 (1972), ibid, vol. 94, P. 1410 (1972) and ibid, vol. 95, P. 2401 (1973). None of these compounds cited therein, however, have been put into practice because they have not an excellent antibacterial action to a satisfactory extent against both Gram-positive and Gram-negative bacteria.

It is thus an object of the present invention to provide a new class of 7α-methoxycephalosporin derivatives which have an excellent antibacterial activity. It is another object of this invention to provide processes for the preparation of such 7α-methoxycephalosporin derivatives.

In accordance with the present invention, there are provided 7α-methoxycephalosporin derivatives having the formula

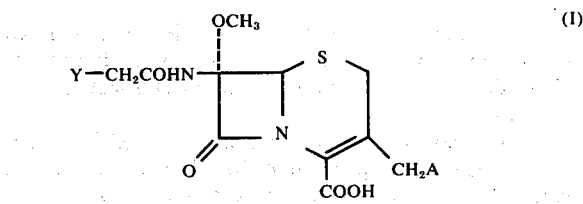

wherein A represents acetoxy group, carbamoyloxy group or (1-methyl-1H-tetrazol-5-yl) thio group and Y represents propargylthio group, azidomethylthio group, 2-hydroxyethylthio group, 3-isoxazolyloxy group, 3-isoxazolythio group, methylsulfonyl group, ethylsulfonyl group, cyanoethylsulfonyl group of sydnon-3-yl group and the nontoxic pharmaceutically acceptable salts thereof, including their alkali or alkaline earth metal salts such as the sodium, potassium, calcium or aluminum salt, the ammonium salt and the substituted ammonium salts such as the triethylamine, dicyclohexylamine, procaine, dibenzylamine or N-ethylpiperidine salt.

Compounds of the formula (I) which are preferred are those wherein Y is 2-hydroxyethylthio group, methylsulfonyl group, ethylsulfonyl group, 2-cyanoethylsulfonyl and sydnon-3-yl group.

Most preferable compounds of this invention are as follows:

7β-ethylsulfonylacetamido-7α-methoxy-3-(1-methyl-1H-tetrazol-5-yl)thiomethyl-3-cephem-4-carboxylic acid, 7α-methoxy-7β-methylsulfonylacetamido-3-(1-methyl-1H-tetrazol-5-yl)thiomethyl-3-cephem-4-carboxylic acid, 7α-methoxy-3-(1-methyl-1H-tetrazol-5-yl)thiomethyl-7β-(sydnon-3-acetamido)-3-cephem-4-carboxylic acid, 7β-(2-hydroxyethyl)thioacetamido-7α-methoxy-(1-methyl-1H-tetrazol-5-yl)thiomethyl-3-cephem-4-carboxylic acid, 7β-(2-cyanoethylsulfonyl)acetamido-7α-methoxy-3-(1-methyl-1H-tetrazol-5-yl)thiomethyl-β-cephem-4-carboxylic acid, The present invention also provides a process for the preparation of the 7α-methoxycephalosporin derivatives of the formula (I) and a nontoxic pharmaceutically acceptable salt thereof which comprises reacting a compound having the formula

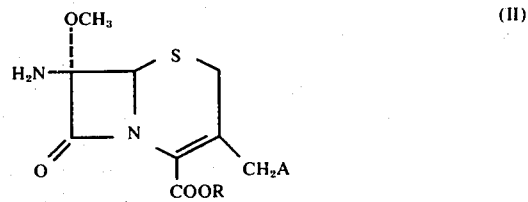

wherein R represents a protective group for a carboxyl group and A has the same meaning as defined above with a carboxylic acid having the formula

wherein Y has the same meaning as defined above or the reactive derivative thereof to give a compound having the formula

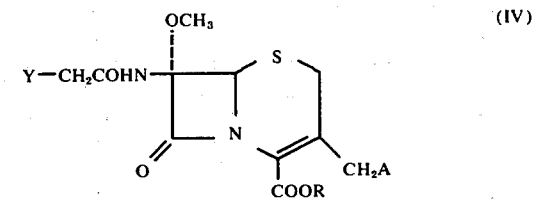

wherein A, R and Y have the same meanings as defined above and removing the protective group for the carboxyl group from said compound.

In the first step of preparing the compounds represented by the formula (I), the compound represented by the formula (II) is reacted with a carboxylic acid represented by the formula (III) or the reactive derivative thereof. In the above reaction, the reaction derivatives of the carboxylic acid represented by the formula (III) include a halide of the acid (III), e.g., the chloride or bromide; a mixed acid anhydride of the acid (III) with an alkyl phosphate such as methyl phosphate or ethyl phosphate, an alkyl carbonate such as methyl carbonate or ethyl carbonate or an aliphatic carboxylic acid such as pivalic acid or pentanoic acid; an anhydride of the acid (III); and an amide of the acid (III) with imidazole or triazole.

The halide of the acid (III) can be most preferably employed.

In the above formula, the protective group for a carboxyl group include benzyl group, p-methoxybenzyl group, benzhydryl group, a tertiary alkyl group, e.g., tert.-butyl or tert.-amyl, an alkoxymethyl group e.g., benzyloxymethyl or methoxymethyl, phenacyl group e.g., phenacyl or p-bromophenacyl, and polyhalogenated ethyl group, e.g., 2,2,2-trichloroethyl, preferably benzhydryl group.

The reaction is carried out in an inert organic solvent at temperatures of from about −10° C. to about 30° C., preferably at about 0° C.

Suitable reaction media are inert organic solvents such as chloroform, methylene chloride, ethylene chloride, acetone, acetnitrile, ethyl acetate, ethyl formate, tetrahydrofuran, ether and dioxane.

When the free carboxylic acid represented by the formula (III) is used in the above reaction, the reaction is carried out in the presence of a condensing agent such as N,N'-dicyclohexylcarbodiimide or N,N'-diethylcarbodiimide. When the halide of the carboxylic acid represented by the formula (III) is used, the reaction is carried out in the presence of a base such as alkali metal bicarbonates, e.g., sodium bicarbonate, potassium bicarbonate, alkali metal carbonate, e.g., sodium carbonate, potassium carbonate, trialkylamines, e.g., trimethylamine, triethylamine, dialkylanilines, e.g., dimethylaniline, diethylaniline or pyridine.

After completion of the reaction, the desired product (IV) may be recovered by a conventional means. For example, the reaction mixture is washed with water and dried with a suitable drying agent, e.g., anhydrous sodium sulfate. The reaction solvent is distilled off and, if desired, the residue is purified with chromatography.

the removing step of the carboxyl-protecting group may be carried out by a conventional means. For instance, when the protective group is benzhydryl, tertiary alkyl, p-methoxybenzyl or alkoxymethyl, the step may be conducted by contacting the compound (IV) with a strong acid such as a triahalogenated acetic acid, e.g., trifluoroacetic acid, trichloroacetic acid or a mineral acid, e.g., hydrochloric acid, hydrobromic acid. The reaction is carried out in the presence of an inert organic solvent such as chloroform, dichloromethane, dichloroethane, benzene, toluene, chlorobenzene or anisole, preferably anisole or dichloroethane, at temperatures of from 0° to 30° C.

When the protective group is benzyl, p-methoxybenzyl, phenacyl or 2,2,2-trichloroethyl, the compound (IV) is subjected to catalytic reduction or to reduction with a suitable reducing agent such as zinc or tin in acetic acid. After completion of the reaction, the desired product may be recovered by a conventional means. For example, the reaction mixture is extracted with an aqueous weakly basic solution, e.g., potassium secondary phosphate or sodium bicarbonate solution. The extract is made acidic and extracted with a suitable solvent. The solvent is distilled off to give the desired product.

When the carboxylic acid having the formula (III) wherein Y is 2-hydroxyethylthio group are used, it is preferred to protect the hydroxyl group with a suitable group such as 2-tetrahydropyranyl group or alkoxyalkyl group, e.g., methoxymethyl, ethoxyethyl and to remove the protective group from the hydroxy group after the reaction of the carboxylic acid (III) with the compound (II) by a conventional means.

Alternatively, the compound having the formula (I) wherein A is (1-methyl-1H-tetrazol-5-yl)thio group can be prepared by reacting the compound having the formula (I) wherein A is acetoxy group or carbamoyloxy group with 5-mercapto-1-methyl-1H-tetrazol. The reaction is carried out at neutral conditions, i.e., at a range of pH 6.5 – 7.5 in the presence of water or an aqueous organic solvent such as an aqueous methanol, ethanol, acetone or dioxane solution at a temperature of from about 50° to 100° C. The reaction is preferably carried out in buffer solution of pH 6.5 – 7.5. After completion of the reaction, the desired product can be recovered by a conventional means. For instance, the reaction mixture is made acidic and extracted with a suitable solvent. The extract is purified by chlomatography.

The compounds of the formula (I) thus obtained can be converted to a nontoxic pharmaceutically acceptable salt thereof by a conventional neutralization procedures.

The compounds of this invention have useful antibacterial properties. In particular, they show in vitro and in vivo activity against Gram-positive and Gram-negative bacterial and are accordingly valuable as antibacterial agents.

Minimum inhibitory concentrations (MIC) were determined for the compounds of this invention. The results are reported in Table I.

Table I

Minimum Inhibitory Concentration (mcg/ml)

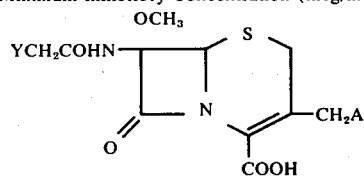

| Y | A | S.aureus 209p | S.aureus R | E. coli NIHJ | Sh. flexneri 609 (R) | Klebsiella 2a | Klebsiella 806 | Klebsiella 846 | Prot. vulgaris | Salm. ent. Gaertner |
|---|---|---|---|---|---|---|---|---|---|---|
| (β-lactam oxazole structure) | (tetrazole-thio structure with CH₃) | 0.8 | 1.5 | 1.5 | 1.5 | 1.5 | 1.5 | >200 | 6.2 | 0.8 |
| $CH_3SO_2-$ | " | 0.8 | 3.1 | 1.5 | 1.5 | 1.5 | 0.8 | 400 | 12.5 | 0.4 |
| $HOCH_2CH_2S-$ | " | 0.8 | 1.5 | 1.5 | 1.5 | 3.1 | 1.5 | 400 | 6.2 | 1.5 |
| $C_2H_5SO_2-$ | " | 1.5 | 1.5 | 1.5 | 1.5 | 1.5 | 1.5 | >400 | 6.2 | 0.8 |
| $NCCH_2CH_2SO_2-$ | " | 1.5 | 3.1 | 1.5 | 1.5 | 3.1 | 1.5 | 200 | 6.2 | 0.8 |
| $HC\equiv CCH_2S-$ | " | 0.2 | 0.8 | 3.1 | 3.1 | 3.1 | 3.1 | 400 | 3.1 | 0.8 |
| $N_3CH_2S-$ | " | 0.4 | 0.4 | 3.1 | 3.1 | 1.5 | 3.1 | >200 | 1.5 | 0.8 |

Table I-continued

Minimum Inhibitory Concentration (mcg/ml)

$$YCH_2COHN-\underset{O}{\overset{OCH_3}{\diagdown}}\underset{\overset{|}{COOH}}{\overset{S}{\diagup}}CH_2A$$

| Y | A | S.aureus 209p | S.aureus R | E.coli NIHJ | E.coli 609 (R) | Sh. flexneri 2a | Klebsiella 806 | Klebsiella 846 | Prot. vulgaris | Salm. ent. Gaertner |
|---|---|---|---|---|---|---|---|---|---|---|
| isoxazolyl-O— | methylthio-triazolyl | 0.2 | 0.8 | 3.1 | 3.1 | 3.1 | 3.1 | >400 | 6.2 | 1.5 |
| isoxazolyl-S— | " | 0.2 | 0.8 | 3.1 | 3.1 | 3.1 | 6.2 | >400 | 3.1 | 0.8 |
| $N_3CH_2S$— | $OCONH_2$ | 0.2 | 1.5 | 3.1 | 6.2 | 3.1 | 3.1 | >400 | 3.1 | 1.5 |
| isoxazolyl-S— | $OCOCH_3$ | 0.2 | 0.8 | 3.1 | 6.2 | 6.2 | 3.1 | >400 | 3.1 | 1.5 |
| $C_6H_5$— | $OCONH_2$ | 0.8 | 3.1 | 25 | 25 | 12.5 | 25 | >400 | 25 | 12.5 |
| Cephalothin | | ≤0.1 | ≤0.1 | 6.2 | 25 | 12.5 | 6.2 | >200 | 6.2 | 6.2 |

It would be evident from the data given above that the compounds of this invention exhibit more active effect against Gram-positive and, especially, Gram-negative bacteria than known cephalosporin derivatives.

In the treatment of infection in human, the compounds of this invention are administered orally or parenterally in accordance with conventional procedures antibiotic administration, for example, in the form of tablets, capsules, injectable liquids and suspensions. Usually, injectable liquids are preferred. The dosage may be varied depending upon ages, condition and weight of a patient. The compound is usually administered in an amount of from about 250 mg. to about 3000 mg. per day for adult in divided dosage, e.g., three or four times a day.

The carboxylic acids represented by the formula (III) wherein Y is propargylthio, azidomethylthio, 2-hydroxyethylthio, 3-isoxazolylthio, 3-isoxazolyloxy and 2-cyanoethylsulfonyl or reactive derivatives thereof are novel and can be prepared as follows:

Preparation of the carboxylic acids (III) or reactive derivatives thereof

1. Azidomethylthioacetic acid

After stirring a mixture of 6.7 g. of ethyl chloromethylthioacetate, 5 g. of sodium azide and 15 ml. of dimethylformamide for 17 hours at 45° C., the reaction mixture was diluted with 150 ml. of ether, followed by washing with water for three times. By drying the ether layer over magnesium sulfate and then distilling it under reduced pressure, 6.1 g. of ethyl azidomethylthioacetate was obtained as a liquid having a boiling point of 77° – 80° C. (3 mm Hg.).

A mixture of 7 g. of the ester and 22 ml. of a 20% aqueous solution of potassium hydroxide was stirred for 2 hours at room temperature, and then was adjusted to about pH 2.0 with hydrochloric acid with ice-cooling. The mixture was subjected to extraction with methylene chloride for three times. By drying the extract over magnesium sulfate and then removing the solvent therefrom, was obtained in a quantitative yield azidomethylthioacetic acid in the form of a colorless liquid.

2. Propargylthioacetyl chloride

To 3 g. of propargylthioacetic acid were added 10 ml. of anhydrous benzene and 2.3 ml. of thionyl chloride, and the mixture was stirred in an oil-bath heated to 60° – 65° C. for 3 hours. After allowing the mixture to cool, the solvent was removed therefrom. The resulting residue was distilled under reduced pressure to produce 2.9 g. of a pale yellow liquid having a boiling point of 73° C. (8 mm Hg.).

3. 3-Isoxazolyloxyacetyl chloride

In 200 ml. of dimethylformamide was dissolved 18.0 g. of 3-hydroxyisoxazole. To the solution was added 8.5 g. of powdery sodium hydroxide, followed by stirring for 6 hours at room temperature. Then, 33.6 g. of ethyl bromoacetate was dropwisely added to the mixture with ice-cooling. After allowing the mixture to stand at room temperature overnight, it was poured into 1 l. of ice water. The resulting mixture was subjected to extraction with 3 l. of diethyl ether, followed by washing the ether-layer with water and drying it over anhydrous sodium sulfate. By distilling the oily substance obtained by the removal of the ether, was obtained 16.4 g. of colorless oily product of ethyl 3-isoxazolyloxyacetate having a boiling point of 70° – 74° C./2 mmHg. (oil bath temperature).

The ester 1.0 g. was suspended in 5 ml. of a 5% solution of sodium hydroxide, followed by stirring for 30 minutes at room temperature. The suspension was made acidic (pH 1) with a concentrated hydrochloric acid, followed by extraction with 150 ml. of diethyl ether. By washing the ether layer with water, drying the layer over anhydrous sodium sulfate, removing the ether therefrom and subjecting the resulting solid to recrystallization with isopropyl ether, was obtained 0.61 g. of colorless prism-like product of 3-isoxazolyloxyacetic acid melting at 154° – 155° C.

The 3-isoxazolyloxyacetic acid 2.0 g. was added to Vilsmeier reagent which had been prepared by dissolving 1.38 g. of dimethylformamide in 150 ml. of diethyl ether and then introducing hosgene into the solution at 0° – 5° C. The mixture was stirred for 1 hour at room temperature and then refluxed for 45 minutes. The insoluble matter was filtered off from the mixture and the ether was removed from the filtrate, followed by adding 150 ml. of n-hexane to the resulting residue to filter off the precipitated insoluble matter. By removing n-hexane from the filtrate and then distilling the resulting oily substance, was obtained 1.78 g. of colorless 3-isoxazolyloxyacetyl chloride boiling at 70° – 75° C/2 mmHg. (oil-bath temperature).

4. 3-Isoxazolylthioacetyl chloride

In 80 ml. of acetonitrile was dissolved 7.0 g. of 2-benzylisoxazoline-3-thion. The solution was added with 9.2 g. of ethyl bromoacetate at room temperature and was stirred for 4 hours, followed by heating for 4 hours to 65° – 70° C. (in an oil-bath) to remove the solvent. By purifying the resulting residue by means of silica gel column (eluted by benzene), was obtained 5.58 g. of pale yellow oily product of ethyl 3-isoxazolylthioacetate, $n_D^{26}$ 1.5013.

The resulting ester 3.33 g. was suspended in 30 ml. of a 5% sodium hydroxide solution. The mixture was stirred for 2.5 hours at room temperature, and then was made acidic (pH 1) with a concentrated hydrochloric acid under ice-cooling condition, followed by extraction with 150 ml. of dichloromethane. The dichloromethane layer was washed with water, and dried over anhydrous sodium sulfate. By subjecting the solid obtained by the removel of dichloromethane from the extract to recrystallization with ligroin, was obtained 2.83 g. of colorless needles of 3-isoxazolylthioacetic acid melting at 72° – 73° C.

460 mg. of 3-isoxazolylthioacetic acid thus obtained was added to Vilsmeier reagent which had been prepared by dissolving 2.48 mg. of dimethylformamide in 60 ml. of diethyl ether and then introducing phosgene into the solution at 0° – 5° C. The mixture was stirred for 1 hour at room temperature and then refluxed for 15 minutes, followed by filtering off insoluble matter and removing the ether from the mixture. By adding to the resulting residue 100 ml. of n-hexane, filtering out the insoluble matter precipitated and then removing n-hexane under reduced pressure (at 20° C), was obtained 440 mg. of pale yellow oily product of 3-isoxazolylthioacetyl chloride, $n_D^{23}$ 1.5400.

5. Tetrahydropyranyl-2-oxyethylthioacetyl chloride

To an acetone solution of 11.7 g. of thioglycol and 25 g. of ethyl bromoacetate was added 12.6 g. of sodium bicarbonate in 100 ml. of water. The solution was stirred overnight at room temperature. The acetone was distilled off under reduced pressure and the residue was extracted with two portions of 100 ml. of ether. The extract was washed twice with water and dried over anhydrous magnesium sulfate. The solvent was distilled off under reduced pressure to give 21.7 g. of ethyl 2-hydroxyethylthioacetate. To 14.2 g. of the compound thus obtained was added 7.26 g. of 2,3-dihydropyran, followed by dissolving 1.65 g. of p-toluenesulfonic acid monohydrate after ice-cooling. The solution was stirred for 2 hours at room temperature and poured into an aqueous sodium bicarbonate. The mixture was extracted with ethyl acetate. The extract was washed with water and dried over anhydrous magnesium sulfate. The solvent was distilled off to give 15.8 g. of ethyl tetrahydropyranyl-2-oxyethylthioacetate as pale yellow oil. To the product was added 63.6 ml. of 1 N sodium hydroxide, followed by stirring for 30 minutes at room temperature. The insolubles were separated off by extraction with chloroform. The layer was made acidic and extracted with ethyl acetate. The extract was dried over anhydrous magnesium sulfate and the solvent was distilled off to give 7 g. of tetrahydropyranyl-2-oxyethylthioacetic acid. In 3.3 g. of the compound thus obtained was dissolved 20 ml. of chloroform free from ethanol. To the solution were added 1.2 ml. of thionylchloride and three drops of dimethyl formamide under ice-cooling, followed by stirring for 2 hours at bath temperature of 50° C. The solvent was distilled off to give tetrahydropyranyl-2-oxyethylthioacetyl chloride.

6. 2-Cyanoethylsulfonylacetyl chloride

To a solution of 5.2 g. of 2-cyanoethylthioacetic acid in 50 ml. of acetic acid was added 12 ml. of 35% hydrogen peroxide at 40° – 50° C. with stirring. The reaction mixture was stirred overnight at room temperature then 2 hours at 50° C. and concentrated under reduced pressure below 40° C. to give colorless solid which was recrystallized from ethylacetate containing small amount of acetone yield 4.3 g. of 2-cyanoethylsulfonyl acetic acid, m.p. 140° C.

To a suspension of 199 mg. of sodium salt of the above acid in 10 ml. of dry benzene was added 5 ml. of oxalyl chloride and the mixture was refluxed for 1.5 hours. After removal of sodium chloride, concentration of the reaction mixture under reduced pressure gave 2-cyanoethylsulfonylacetyl chloride as oily substance.

The following examples are presented to further illustrate the present invention.

EXAMPLE 1

3-Acetoxymethyl-7β-(3-isoxazolylthioacetamido)-7α-methoxy-3-cephem-4-carboxylic acid a. In 20 ml. of tetrahydrofuran were dissolved 700 mg. of benzhydryl 3-acetoxymethyl-7β-amino-7α-methoxy-3-cephem-4 -carboxylate and 257 mg. of 3-isoxazolylthioacetyl chloride, and to this solution was added dropwise at 0° C., 217 mg. of N,N-diethylaniline in 10 ml. of tetrahydrofuran. The reaction mixture was stirred at room temperature for 15 minutes and concentrated at 20° C. under reduced pressure to about one-half of its initial volume. The residue was dissolved in 150 ml. of ethyl acetate, washed successively with 30 ml. of a 5% aqueous potassium dihydrogen phosphate solution, 30 ml. of a 50% aqueous sodium hydrogen carbonate solution and two portions of 50 ml. of a 20% aqueous sodium chloride solution, and dried over anhydrous sodium sulfate. The solvent was distilled off under reduced pressure, and the residue was purified by means of silica gel chromatography (eluent; ethyl acetate - benzene, 1 : 4) to yield 331 mg. of benzhydryl 3-acetoxymethyl-7β-(3-isoxazolythioacetamido)-7α-methoxy-3-cephem-4-carboxylate as a white powder, m.p. 63° – 66° C.

TLC (silica gel) : eluent; ethyl acetate - benzene (1 : 3) Rf = 0.37
IR spectrum $\nu_{max}$ cm$^{-1}$ (Nujol)

-continued 3240, 1778, 1720, 1700
UV spectrum   λ_max mμ        (MeOH)
   264 (ε=7000)
NMR spectrum   δppm           (CDCl₃)

8.35  (1H, doublet, isoxazole H)

6.95 – 7.37 (11H, multiplet, two φ and —CONH)
7.03      (1H, singlet, —O—CH< at 4-position)

6.32  (1H, doublet, isoxazole H)

5.06 (1H, singlet, C—H at 6-position)
4.70 – 5.22 (2H, couple of doublet, —CH₂—O—at 3-position)
3.52 (2H, singlet, —SCH₂CO—)
3.50 (3H, singlet, O—CH₃ at 7-position)
3.00 – 3.63 (2H, couple of doublet, CH₂ at 2-position)
1.98 (3H, singlet, —OCOCH₃ at 3-position)

Elementary analysis for $C_{29}H_{27}N_3O_8S_2$

Calcd. (%) : C,57.13; H,4.46; N,6.89.
Found (%) : C,57.35; H,4.58; N,6.71.

b. In 1.0 ml. of anisole was dissolved 250 mg. of the compound obtained above, and to this solution was added under ice-cooling 1.0 ml. of trifluoroacetic acid. The mixture was stirred for 30 minutes under the same conditions as above. The reaction mixture was concentrated under reduced pressure at room temperature. The residue was dissolved in 10 ml. of ethyl acetate and extracted with a 10% aqueous dipotassium hydrogenphosphate solution. The extract was washed with ethyl acetate and made to pH 2.0 by addition of 3N hydrochloric acid under cooling. The precipitate was extracted with ethyl acetate, and the extract was dried over anhydrous sodium sulfate. Upon distilling off the solvent under reduced pressure, there was obtained 60 mg. of 3-acetoxymethyl-7β-(3-isoxazolylthioacetamido)-7α-methoxy-3-cephem-4-carboxylic acid as a power, m.p. 130° – 132° C. (decom.)

TLC (silica gel): eluent; methanol - chloroform (1:4)
Rf = 0.34
IR spectrum   ν_max cm⁻¹    (Nujol)
   3500, 3270, 1780, 1730, 1700
UV spectrum   λ_max mμ   (pH 6.8 buffer solution)
   261 (ε = 8000)
NMR spectrum   δppm   (DMSO-d₆)
9.34 (1H, singlet, CONH at 7-position)

8.63  (1H, doublet, isoxazole H)

6.34  (1H, doublet, isoxazole H)

5.15 (1H, singlet, C—H at 6-position)
5.12 – 4.64 (2H, couple of doublet, —CH₂—O—at 3-position)
5.01 (2H, singlet, —S—CH₂—CO—)
3.68 – 3.14 (2H, couple of doublet, —H₂ at 2-position)
3.43 (3H, singlet, O—CH₃ at 7-position)

2.02 (3H, singlet, —COCH₃ at 3-position)

Elementary analysis for $C_{16}H_{17}O_8N_3S_2$

Calcd. (%) : C,43.34; H,3.86; N,9.43.
Found (%) : C,43.21; H,3.70; N,9.52.

Following compounds were obtained in the same manner as in the above Examples.

IR spectrum   ν_max cm⁻¹        (Nujol)
   3500, 3300, 1778 (Sh), 1764, 1720 (Sh), 1702
UV spectrum   λ_max mμ   (pH 6.8 buffer solution)
   272 (ε = 9700)
NMR spectrum   δppm   (DMSO-d₆)

3.41          (3H, singlet, OCH₃ at 7-position)
3.86          (3H, singlet, N—CH₃)
3.15 – 3.60   (2H, quartet, H₂ at 2-position)
4.46 – 4.08   (2H, quartet, —CH₂S— at 3-position)
4.80          (2H, singlet, —O—CH₂CON)
5.13          (1H, singlet, H at 6-position)
6.34          (1H, doublet, H of isoxazole nucleus)
8.64          (1H, doublet, H of isoxazole nucleus)

NMR spectrum   δ ppm   (DMSO-d₆)

3.20          (1H, triplet, HC≡C—)
around 3.5    (9H, multiplet, OCH₃ at 7-position,
              H₂ at 2-position, —CH₂—S—CH₂—CO—)
3.90          (3H, singlet, N—CH₃)
4.2 – 4.3     (2H, quartet, —CH₂—S— at 3-position)
5.05          (1H, singlet, OH at 6-position)

NMR spectrum   δppm   (d₆-acetone)

3.40          (2H, singlet, —SCH₂CO)
3.46 – 3.50   (2H, quartet, H₂ at 2-position)
3.50          (3H, singlet, OCH₃ at 7-position)
3.98          (3H, singlet, N—CH₃)
4.1 – 4.5     (2H, quartet, —CH₂S— at 3-position)
4.39          (2H, singlet, N₃CH₂S—)
5.02          (1H, singlet, H at 6-position)

EXAMPLE 2

7β-Azidomethylthioacetamido-3-carbamoyloxymethyl-7α-methoxy-3-cephem-4-carboxylic acid To the solution of 250 mg. of benzhydryl 7β-amino-3-carbamoyloxymethyl-7α-methoxy-3-cephem-4-carboxylate in 8 ml. of methylene chloride, 80 mg. of N,N-diethylaniline was added with ice-cooling and stirring, and then a solution of 90 mg. of azidomethylthioacetyl chloride in 1 ml. of methylene chloride was added to the solution. The mixture was stirred for 1 hour. The reaction mixture was washed with an aqueous solution of sodium bicarbonate and then with water, followed by drying over anhydrous magnesium sulfate. After removing the solvent from the mixture, the residue was purified by means of preparative silica gel chromatography (20 cm × 20 cm, 0.2 cm in thickness; eluted by ethyl acetate - benzene (1 : 2) mixture) to obtain 120 mg. of colorless powder of benzhydryl 7β-azidomethylthioacetamido-3-carbamoyloxy-methyl-7α-methoxy-3-cephem-4-carbaxylate. By treating the ester thus obtained in the same way as described in Example 1 using 2 ml. of anisole and 1 ml. of trifluoroacetic acid, there produced 60 mg. of powdery 7β-azidomethylthioacetamido-3-carbamoyloxymethyl-7α-methoxy-3-cephem-4-carboxylic acid.

| IR spectrum | $\nu$ max cm$^{-1}$ | (KBr) |
|---|---|---|
| 3300 – 3500, 2100, 1780, 1715, 1680 | | |
| UV spectrum | $\lambda$ max m$\mu$ | (a buffer solution of pH 6.8) |
| 245 ($\epsilon$ = 8100), 267 ($\epsilon$ = 8500) | | |
| NMR spectrum | $\delta$ ppm | (CD$_3$CN) |
| 3.41 | (2H, singlet, SCH$_2$CO—) | |
| 3.47 – 3.50 | (2H, quartet, H$_2$ at 2-position) | |
| 3.50 | (3H, singlet, OCH$_3$ at 7-position) | |
| 4.40 | (2H, singlet, N$_3$—CH$_2$S—) | |
| 4.82 | (2H, singlet, —CH$_2$OCO— at 3-position) | |
| 5.03 | (1H, singlet, H at 6-position) | |

Elementary analysis for $C_{13}H_{16}N_6O_7S_2$

Calcd. (%) : C,36.10; H,3.73; N,19.44.
Found (%) : C,35.81; H,3.95; N,19.11.

EXAMPLE 3

7α-Methoxy-7β-methylsulfonylacetamido-3-(1-methyl-1H-tetrazol-5-yl)thiomethyl-3-cephem-4-carboxylic acid a. In 5 ml. of dichloroethane was dissolved 525 mg. of benzhydryl 7β-amino-7α-methoxy-3-(1-methyl-1H-tetrazol-5-yl)thiomethyl-3-cephem-4-carboxylate and cooled below 0° C. with a freezing mixture. To the solution were added 160 mg. of N,N-diethylaniline and a solution of 165 mg. of methylsulfonylacetyl chloride in 2 ml. of dichloroethane and the mixture was stirred for 1 hour. The reaction mixture was diluted with an adequate amount of ethyl acetate and washed successively with an aqueous potassium hydrogen sulfate solution, a sodium hydrogen carbonate solution and water and dried over anhydrous magnesium sulfate. The solvent was distilled off to give benzhydryl 7α-methoxy-7β-methylsulfonylacetoamido-3-(1-methyl-1H-tetrazol-5-yl)thiomethyl-3-cephem-4-carboxylate as an oil. This oil was subjected to preparative thin layer chromatography (20 × 20 × 0.2 cm; 2 plates) using a mixture of ethyl acetate - benzene (1 : 1) as eluent and purified to give 200 mg. of yellow powders.

| NMR spectrum | $\delta$ ppm | (CDCl$_3$): |
|---|---|---|
| 3.03 | (3H, singlet, CH$_3$SO$_2$—) | |
| 3.50 | (5H, doublet, OCH$_3$ at 7-position and H$_2$ at 2-position) | |
| 3.75 | (3H, singlet, N—CH$_3$) | |
| 4.02 | (2H, singlet, —SO$_2$CH$_2$—CO—) | |
| 4.25 | (2H, quartet, —CH$_2$S— at 3-position) | |
| 5.02 | (1H, singlet, H at 6-position) | |
| 6.86 | (1H, singlet, COOCH$\Phi_2$) | |
| 7.35 | (10H, singlet, two C$_6$H$_5$) | | b. In 2 ml. of anisole was dissolved 200 mg. of the benzhydryl ester obtained by the above process a) and to the solution 1 ml. of trifluoroacetic acid was added under cooling with stirring and the mixture was kept on stirring under cooling for 30 minutes and allowed to stand at room temperature for further 10 minutes. The solvent was distilled off and the residue was dissolved in ethyl acetate and the solution was extracted with 10% aqueous potassium hydrogen phosphate solution. The extract was washed with ethyl acetate and adjusted to pH 2 with 10% hydrochloric acid and the carboxylic acid thus obtained was extracted with ethyl acetate. The extract was dried over anhydrous magnesium sulfate and the solvent was distilled off to give 110 mg. of 7α-methoxy-7β-methylsulfonylacetamido-3-(1-methyl-1H-tetrazol-5-yl)thiomethyl-3-cephem-4-carboxylic acid as amorphous powders.

| Thin layer chromatography (silica-gel) | | |
|---|---|---|
| eluent : n-butanol : acetic acid : water (4:1:1) Rf = 0.26 | | |
| NMR spectrum | $\delta$ppm | (d$_6$-acetone) |
| 3.07 | (3H, singlet, C$_3$SO$_2$—) | |
| 3.45 | (3H, singlet, OCH$_3$ at 7-position) | |
| 3.62 | (2H, quartet, H$_2$ at 2-position) | |
| 3.92 | (3H, singlet, N—CH$_3$) | |
| 4.18 | (2H, singlet, —SO$_2$CH$_2$CO—) | |
| 4.35 | (2H, quartet, —CH$_2$S— at 3-position) | |
| 5.06 | (1H, singlet, H at 6-position) | |
| 8.60 | (1H, singlet, CONH at 7-position) | |

Elementary analysis for $C_{14}H_{18}O_7N_6S_3$

Calcd. (%) : C,35.14; H,3.80; N,17.56.
Found (%) : C,34.87; H,4.01; N,17.88.

Potassium 7α-methoxy-7β-methylsulfonylacetamido-3-(1-methyl-1H-tetrazol-5-yl)thiomethyl-3-cephem-4-carboxylate 7α-Methoxy-7β-methylsulfonylacetamido-3-(1-methyl-1H-tetrazol-5-yl)thiomethyl-3-cephem-4-carboxylic acid 500 mg. was dissolved in an equimolar amount of a 5% aqueous potassium bicarbonate. The solution was subjected to freeze-drying to 520 mg. of the desired salt as amorphous powder.

EXAMPLE 4

7β-Ethylsulfonylacetamido-7α-methoxy-3-(1-methyl-1H-tetrazol-5-yl)thiomethyl-3-cephem-4-carboxylic acid a. In the same manner as in the Example 3, reaction of 525 mg. of benzhydryl 7β-amino-7α-methoxy-3-(1-methyl-1H-tetrazol-5-yl)thiomethyl-3-cephem-4-carboxylate and 180 mg. of ethylsulfonylacetyl chloride gave 430 mg. of benzhydryl 7β-ethylsulfonylacetamido-7α-methoxy-3-(1-methyl-1H-tetrazol-5-yl)thiomethyl-3-cephem-4-carboxylate as pale yellow powders.

| NMR spectrum | $\delta$ppm | (CDCl$_3$) |
|---|---|---|
| 1.32 | (3H, triplet, CH$_3$CH$_2$SO$_2$—) | |
| 3.27 | (2H, quartet, CH$_3$CH$_2$SO$_2$—) | |
| 3.50 | (3H, singlet, OCH$_3$ at 7-position) | |
| 3.55 | (2H, quartet, H$_2$ at 2-position) | |
| 3.90 | (3H, singlet, N—CH$_3$) | |
| 4.03 | (2H, singlet, —SO$_2$CH$_2$CO—) | |
| 4.25 | (2H, quartet, —CH$_2$S— at 3-position) | |
| 5.03 | (1H, singlet, H at 6-position) | |
| 6.88 | (1H, singlet, COOCH$\Phi_2$) | |
| 7.35 | (10H, singlet, two C$_6$H$_5$) | | b. In the usual manner, hydrolysis of 300 mg. of the above benzhydryl ester with 1.5 ml. of trifluoroacetic acid in 3 ml. of anisole gave 140 mg. of 7β-ethylsulfonylacetamido-7α-methoxy-3-(1-methyl-1H-tetrazol-5-yl)thiomethyl-3-cephem-4-carboxylic acid as colorless powders.

| NMR spectrum | δ ppm | (d₆-acetone) |
|---|---|---|
| 1.34 | (3H, triplet, CH₃CH₂SO₂—) | |
| 3.29 | (2H, quartet, CH₃CH₂SO₂—) | |
| 3.51 | (3H, singlet, OCH₃ at 7-position) | |
| 3.69 | (2H, quartet, H₂ at 2-position) | |
| 3.98 | (3H, singlet, N—CH₃) | |
| 4.18 | (2H, singlet, —SO₂CH₂CO—) | |
| 4.40 | (2H, quartet, CH₂S— at 3-position) | |
| 5.07 | (1H, singlet, H at 6-position) | |
| 8.66 | (1H, singlet, —CONH— at 7-position) | |

EXAMPLE 5

7β-(2-Cyanoethylsulfonyl)acetamido-7α-methoxy-3-(1-methyl-1H-tetrazol-5-yl)thiomethyl-3-cephem-4-carboxylic acid a. In the same manner as in the Example 3, acylation of 525 mg. of benzhydryl 7β-amino-7α-methoxy-3-(1-methyl-1H-tetrazol-5-yl)thiomethyl-3-cephem-4-carboxylate with 205 mg. of (2-cyanoethylsulfonyl)acetyl chloride in the presence of 160 mg. of N,N-diethylaniline gave 380 mg. of benzhydryl 7β-(2-cyanoethylsulfonyl)acetamido-7α-methoxy-3-(1-methyl-1H-tetrazol-5-yl)thiomethyl-3-cephem-4-carboxylate as yellowish powders.

| NMR spectrum | δ ppm | (CDCl₃) |
|---|---|---|
| 2.90 | (2H, triplet NCCH₂CH₂SO₂—) | |
| 3.55 | (3H, singlet, OCH₃ at 7-position) | |
| 3.50 – 3.70 | (4H, multiplet, H₂ at 2-position and NCCH₂CH₂SO₂—) | |
| 3.75 | (3H, singlet, N—CH₃) | |
| 4.10 – 4.40 | (4H, multiplet, CH₂S—at 3-position and SO₂CH₂CO—) | |
| 5.05 | (1H, singlet, H at 6-position) | |
| 6.88 | (1H, singlet, COOCHφ₂) | |
| 7.35 | (10H, singlet, two C₆H₅) | | b. In the usual manner, hydrolysis of 300 mg. of the above benzhydryl ester with 1.5 ml. of trifluoroacetic acid in 3 ml. of anisole gave 130 mg. of 7β-(2-cyanoethylsulfonyl)-acetamido-7α-methoxy-3-(1-methyl-1H-tetrazol-5-yl)thiomethyl-3-cephem-4-carboxylic acid as colorless powders.

| NMR spectrum | δ ppm | (d₆-acetone) |
|---|---|---|
| 3.03 | (2H, triplet, NCCH₂CH₂SO₂—) | |
| 3.40 – 3.85 | (4H, multiplet, H₂ at 2-position and NCCH₂CH₂SO₂—) | |
| 3.50 | (3H, singlet, OCH₃ at 7-position) | |
| 3.94 | (3H, singlet, N—CH₃) | |
| 4.10 – 4.50 | (4H, multiplet, CH₂S— at 3-position and —SO₂CH₂CO—) | |
| 5.06 | (1H, singlet, H at 6-position) | |

EXAMPLE 6

7α-Methoxy-3-(1-methyl-1H-tetrazol-5-yl)thiomethyl-7β-(sydnon-3-acetamido-3-cephem-4-carboxylic acid Following the same procedure as in Example 3 except that 173 mg. of sydnon-3-acetyl chloride was used instead of methylsulfonylacetyl chloride, 60 mg. of 7β-(sydnon-3-acetamido)-7α-methoxy-3-(1-methyl-1H-tetrazol-5-yl)thiomethyl-3-cephem-4-carboxylic acid was obtained.

| NMR spectrum | δ ppm | (d₆-acetone) |
|---|---|---|
| 3.54 | (3H, singlet, OCH₃ at 7-position) | |
| 3.70 | (2H, quartet, H₂ at 2-position) | |
| 3.98 | (3H, singlet, N—CH₃) | |
| 4.42 | (2H, quartet, CH₂S— at 3 position) | |
| 5.12 | (1H, singlet, H at 6-position) | |
| 5.50 | (2H, singlet, —CH₂CONH) | |
| 6.80 | (1H, singlet, H at sydnon ring) | |

Thin layer chromatography (silica-gel):
Developing agent : n-butanol : acetic acid : water (4:1:1)
Rf = 0.31

EXAMPLE 7

7β-(2-Hydroxyethyl)thioacetamido-7α-methoxy-3-(1-methyl-1H-tetrazol-5-yl)thiomethyl-3-cephem-4-carboxylic acid a. In 10 ml. of dichloroethane were dissolved 262 mg. of benzhydryl 7β-amino-7α-methoxy-3-(1-methyl-1H-tetrazol-5-yl)-thiomethyl-3-cephem-4-carboxylate and 80 mg. of N,N-diethylaniline. To the solution was added 5 ml. of dichloroethane containing 120 mg. of tetrahydropyranyl-2-oxyethylthioacetyl chloride under cooling with a freezing mixture and the mixture was stirred for 30 minutes. The reaction mixture was diluted with an adequate amount of ethyl acetate, washed successively with an aqueous potassium bisulfate solution, sodium bicarbonate solution and water and then dried over anhydrous magnesium sulfate. The solvent was distilled off and the residue obtained was purified by means of preparative silica gel chromatography (20 × 20 × 0.2 cm, 2 plates) to give 210 mg. of benzhydryl 7α-methoxy-3-(1-methyl-1H-tetrazol-5-yl)thiomethyl-7β-(tetrahydropyranyl-2-oxyethyl)-thioacetamido-3-cephem-4-carboxylate as pale yellow powders.

b. In 1 ml. of anisole was dissolved 210 mg. of the compound obtained above. To the solution was added 1 ml. of trifluoroacetic acid under ice-cooling, followed by leaving to stand for 5 minutes at room temperature. The large portion of the solvent was distilled off under reduced pressure and the residue was dissolved in a mixture of 20 ml. of ethyl acetate and 10 ml. of a 10% aqueous dipotassium hydrogenphosphate solution. The organic layer was extracted with 5 ml. of a 10% aqueous dipotassium hydrogenphosphate solution and the extract was combined with the aqueous layer obtained above, followed by washing with 20 ml. of ethyl acetate. The aqueous layer was extracted with ethyl acetate and the extract was dried over anhydrous magnesium sulfate. The solvent was distilled off and the residue obtained was purified by means of preparative silica gel chromatography [(20 × 20 × 0.2 cm.), eluent; a mixture of n-butanol : acetic acid : water (4:1:1)] to give 55 mg. of 7β-(2-hydroxyethyl)thioacetamido-7α-methoxy-3-(1-methyl-1H-tetrazol-5-yl)thiomethyl-3-cephem-4-carboxylic acid as amorphous powders.

| IR spectrum | ν max cm⁻¹ | (KBr) |
|---|---|---|
| | 1740, 1675 | |
| UV spectrum | λ max mµ | (a phosphate buffer solution of pH 6.86) |
| | 270 (ε = 9450) | |
| NMR spectrum | δppm | (CD₃CN + D₂O) |
| 5.20 | (1H, singlet, H at 6-position) | |
| 4.15 – 4.25 | (2H, quartet, CH₂S —at 3-position) | |
| 3.90 | (3H, singlet, N—CH₃) | |
| 3.44 | (3H, singlet, —OCH₃ 7-position) | |

| | |
|---|---|
| 3.30 | (2H, singlet, S—CH$_2$—CO at 7-position) |
| 3.68 and 2.74 | (4H, triplet, HOCH$_2$CH$_2$S— at 7-position |

EXAMPLE 8

7β-(3-Isoxazolylthioacetamido)-7α-methoxy-3-(1-methyl-1H-tetrazol-5-yl)thiomethyl-3-cephem-4-carboxylic acid To 8 ml. of a phosphate buffer solution (pH 6.8) were added 160 mg. of 3-acetoxymethyl-7β-(3-isoxazolylthioacetamido)-7α-methoxy-3-cephem-4-carboxylic acid and 45 mg. of 5-mercapto-1-methyl-1H-tetrazole, and this mixture was stirred for 15 minutes in a water bath kept at 95° C. After cooling, the reaction mixture was adjusted to pH 2.5 with 2N phosphoric acid and extracted with ethyl acetate. The extract was dried over anhydrous magnesium sulfate, and the solvent was distilled off at room temperature under reduced pressure. The obtained residue was developed on preparative silica gel chromatography [(20 × 20 × 0.2 cm.), eluent ; a mixture of n-butanol : acetic acid : water (4:1:1)]. A portion around Rf = 0.4 was extracted with methanol. The methanol was distilled off at room temperature under reduced pressure to leave a residue. The residue was washed with ethyl acetate, made to pH 2.0 with 10% hydrochloric acid and extracted with ethyl acetate. The extract was dried and concentrated to give 53 mg. of 7β-(3-isoxazolylthioacetamido)-7α-methoxy-3-(1-methyl-1H-tetrazol-5-yl)thiomethyl-3-cephem-4-carboxylic acid.

| NMR spectrum | δ ppm (DMSO-d$_6$) |
|---|---|
| 3.48 | (3H, singlet, OCH$_3$ at 7-position) |
| 3.20 – 3.68 | (2H, quartet, H$_2$ at 2-position) |
| 3.98 | (3H, singlet, N—CH$_3$) |
| 4.1 – 4.5 | (2H, quartet, —CH$_2$S— at 3-position) |
| 5.00 | (2H, singlet, —SCH$_2$CO—) |
| 5.15 | (1H, singlet, H at 6-position) |
| 6.34 | (1H, doublet, H at 4-position of isoxazole) |
| 8.63 | (1H, doublet, H at 5-position of isoxazole) |

There will be shown below the compounds obtained in the same manner as in the above-mentioned examples and their characteristics.

7β-(3-Isoxazolyloxy)acetoamido-7α-methoxy-3-(1-methyl-1H-tetrazol-5-yl)thiomethyl-3-cephem-4-carboxylic acid

| IR spectrum | ν max cm$^{-1}$ (Nujol) |
|---|---|
| | 3500, 3300, 1778 (Sh), 1764, 1720 (Sh), 1702 |

| UV spectrum | λ max mμ | (pH 6.8 buffer solution) |
|---|---|---|
| | | 272 (ε = 9700) |

| NMR spectrum | δ ppm (DMSO-d$_6$) |
|---|---|
| 3.41 | (3H, singlet, OCH$_3$ at 7-position) |
| 3.86 | (3H, singlet, (N—CH$_3$) |
| 3.15 – 3.60 | (2H, quartet, H$_2$ at 2-position) |
| 4.46 – 4.08 | (2H, quartet, —CH$_2$S— at 3-position) |
| 4.80 | (2H, singlet, —O—CH$_2$CON) |
| 5.13 | (1H, singlet, H at 6-position) |
| 6.34 | (1H, doublet, H on isoxazole nucleus) |
| 8.64 | (1H, doublet, H on isoxazole nucleus) |

3-(1-Methyl-1H-tetrazol-5-yl)thiomethyl-7β-propargylthioacetamido-7α-methoxy-3-cephem-4-carboxylic acid

| NMR spectrum | δ ppm (DMSO-d$_6$) |
|---|---|
| 3.20 | (1H, triplet, HC≡C—) |
| around 3.5 | (9H, multiplet, OCH$_3$ at 7-position, H$_2$ at 2-position, —CH$_2$—S—CH$_2$—CO—) |
| 3.90 | (3H, singlet, N—CH$_3$) |
| 4.2 – 4.3 | (2H, quartet, —CH$_2$—S— at 3-position) |
| 5.05 | (1H, singlet, OH at 6-position) |

Elementary analysis for C$_{16}$H$_{18}$O$_5$N$_6$S$_3$

Calcd. (%) : C,40.84; H,3.86; N,17.86.
Found (%) : C,40.58; H,3.95; N,17.81.

EXAMPLE 9

7α-Methoxy-7β-methylsulfonylacetamido-3-(1-methyl-1H-tetrazol-5-yl)thiomethyl-3-cephem-4-carboxylic acid To 7 ml. of phosphate buffer solution of pH 7.0 were added 220 mg. of 3-acetoxymethyl-7β-methylsulfonylacetamido-7α-methoxy-3-cephem-4-carboxylic acid, 120 mg. of 5-mercapto-1-methyltetrazole and 50 mg. of sodium hydrogen carbonate and the mixture was stirred at a bath temperature of 65° – 70° C. for 4.5 hours. After completion of the reaction, the reaction solution was adjusted to pH 5.5 – 6.0 by adding 10% hydrochloric acid, washed with ethyl acetate twice, then adjusted to pH 2.0 – 2.5 and extracted with ethyl acetate. The extract was dried and distilled to give 45 mg. of 7α-methoxy-7β-methylsulfonylacetamido-3-(1-methyl-1H-tetrazol-5-yl)thiomethyl-3-cephem-4-carboxylic acid as amorphous powders.

| NMR spectrum | δppm (DMSO-d$_6$) |
|---|---|
| 3.07 | (3H, singlet, CH$_3$SO$_2$—) |
| around 3.45 | (3H, singlet, OCH$_3$ at 7-position) |
| 3.62 | (2H, quartet, H$_2$ at 2-position) |
| 4.92 | (3H, singlet, N—CH$_3$) |
| 4.18 | (2H, singlet, —SO$_2$CH$_2$C—) |
| 4.35 | (2H, quartet, —CH$_2$S at 3-position) |
| 5.06 | (1H, singlet, H at 6-position) |
| 8.60 | (1H, singlet, —CONH at 7-position) |

EXAMPLE 10

7β-(2-Hydroxyethyl)thioacetamido-7α-methoxy-3-(1-methyl-1H-tetrazol-5-yl)thiomethyl-3-cephem-4-carboxylic acid To 14 ml. of phosphate buffer solution of pH 7.0 were added 420 mg. of 3-acetoxymethyl)-7β-(2-hydroxyethyl)thioacetamido-7α-methoxy-3-cephem-4-carboxylic acid, 232 mg. of 5-mercapto-1-methyl-tetrazole and 168 mg. of sodium hydrogen carbonate and the mixture was stirred at a bath temperature of 65° – 70° C. for 4.5 hours. After completion of the reaction, the reaction mixture was adjusted to pH 5.5 – 6.0 with a 10% hydrochloric acid, washed twice with ethyl acetate, adjusted to pH 2.0 – 2.5 and extracted with ethyl acetate. The solvent was distilled off to give 110 mg. of 7β-(2-hydroxyethyl)thioacetamido-7α-methoxy-3-(1-methyl-1H-tetrazol-5-yl)thioethyl-3-cephem-4-carboxylic acid as colorless powders.

What is claimed is:

1. A compound having the formula

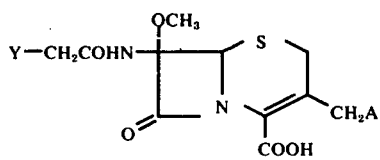

wherein A represents a (1-methyl-1H-tetrazol-5-yl)thio group and Y represents a 2-hydroxy-ethylthio group, a methylsulfonyl group, an ethylsulfonyl group, or a sydnon-3-yl group and a nontoxic pharmaceutically acceptable salt thereof.

2. 7α-Methoxy-7β-methylsulfonylacetamido-3-(1-methyl-1H-tetrazol-5-yl)thiomethyl-3-cephem-4-carboxylic acid.

3. 7β-(2-Hydroxyethyl)thioacetamido-7α-methoxy-3-(1-methyl-1H-tetrazol-5-yl)thiomethyl-3-cephem-4-carboxylic acid.

4. 7β-Ethylsulfonylacetamido-7α-methoxy-3-(1-methyl-1H-tetrazol-5-yl)thiomethyl-3-cephem-4-carboxylic acid.

5. 7α-Methoxy-3-(1-methyl-1H-tetrazol-5-yl)thiomethyl-7β-(sydnon-3-acetamido)-3-cephem-4-carboxylic acid.

* * * * *

UNITED STATES PATENT AND TRADEMARK OFFICE
CERTIFICATE OF CORRECTION

PATENT NO. : 4,007,177  Page 1 of 3
DATED : February 8, 1977
INVENTOR(S) : HIDEO NAKAO et al It is certified that error appears in the above-identified patent and that said Letters Patent are hereby corrected as shown below:

Column 1, line 45:  replace "of" with --- or ---.

Column 3, line 26:  replace "the" with --- The ---.

Columns 3-4 and 5-6, in Table 1:  delete the formula under "Minimum Inhibitory Concentration" and replace with --- 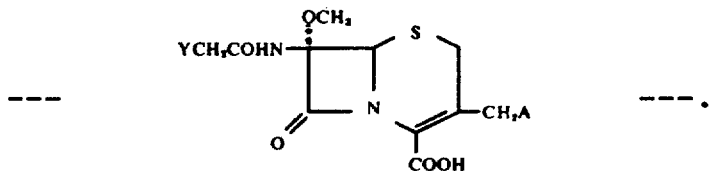 ---.

Column 10, line 12:  before the table, insert the following
--- 7β-(3-Isoxazolyloxy)acetamido-7α-methoxy-3-(1-methyl-1H-tetrazol-5-yl)thiomethyl-3-cephem-4-carboxylic acid ---.

Column 10, line 25:  before the table, insert the following
--- 3-(1-Methyl-1H-tetrazol-5-yl)thiomethyl-7α-methoxy-7β-propargylthioacetamido-3-cephem-4-carboxylic acid ---.

UNITED STATES PATENT AND TRADEMARK OFFICE
CERTIFICATE OF CORRECTION

PATENT NO. : 4,007,177
DATED : February 8, 1977
INVENTOR(S) : HIDEO NAKAO et al

It is certified that error appears in the above–identified patent and that said Letters Patent are hereby corrected as shown below:

Column 10, line 40: before the table, insert the following

--- 7β-Azidomethylthioacetamido-7α-methoxy-3-(1-methyl-1H-tetrazol-5-yl)thiomethyl-3-cephem-4-carboxylic acid ---.

Column 16, line 60: after "3-acetoxymethyl", delete ")".

UNITED STATES PATENT AND TRADEMARK OFFICE
CERTIFICATE OF CORRECTION

PATENT NO. : 4,007,177
DATED : February 8, 1977
INVENTOR(S) : HIDEO NAKAO et al

It is certified that error appears in the above-identified patent and that said Letters Patent are hereby corrected as shown below:

Column 13, lines 60-61: rewrite the compound as
--- 7α-Methoxy-3-(1-methyl-1H-tetrazol-5-yl)-thiomethyl-7β-(sydnon-3-acetamido)-3-cephem-4-carboxylic acid ---.

Column 13, lines 66-67: delete "7β-(sydnon-3-acetamido)-7α-methoxy-3-(1-methyl-1H-tetrazol-5-yl)thiomethyl-3-cephem-4-carboxylic" and replace with
--- 7α-methoxy-3-(1-methyl-1H-tetrazol-5-yl)-thiomethyl-7β-(sydnon-3-acetamido)-3-cephem-4-carboxylic ---.

Signed and Sealed this

Thirteenth Day of November 1979

[SEAL]

Attest:

RUTH C. MASON
Attesting Officer

LUTRELLE F. PARKER
Acting Commissioner of Patents and Trademarks